US005895387A

United States Patent [19]
Guerrero et al.

[11] Patent Number: 5,895,387
[45] Date of Patent: *Apr. 20, 1999

[54] METHOD OF CRANIOFACIAL BONE DISTRACTION

[75] Inventors: Romulo Guerrero, Carvajal 737; Adriana Salazar, both of Quito, Ecuador

[73] Assignee: Romulo Guerrero, Quito, Ecuador

[*] Notice: This patent issued on a continued prosecution application filed under 37 CFR 1.53(d), and is subject to the twenty year patent term provisions of 35 U.S.C. 154(a)(2).

[21] Appl. No.: 08/731,020

[22] Filed: Oct. 9, 1996

[51] Int. Cl.$^6$ ................................. A61B 17/80
[52] U.S. Cl. ..................... 606/71; 606/69; 606/60
[58] Field of Search ...................... 606/71, 70, 69, 606/72, 73, 57, 58, 90, 86, 105, 60

[56] References Cited

U.S. PATENT DOCUMENTS

| | | | |
|---|---|---|---|
| 4,187,841 | 2/1980 | Knutson | 606/105 |
| 4,929,247 | 5/1990 | Rayhack | 606/53 |
| 5,364,396 | 11/1994 | Robinson et al. | 606/53 |
| 5,393,036 | 2/1995 | Sheridan | 606/90 |
| 5,439,465 | 8/1995 | Tumibay | 606/15 |
| 5,540,696 | 7/1996 | Booth, Jr. et al. | 606/88 |
| 5,681,313 | 10/1997 | Diez | 606/69 |

FOREIGN PATENT DOCUMENTS 286136  11/1970  Russian Federation ............ 606/71

*Primary Examiner*—Guy V. Tucker

[57] ABSTRACT

A bone distractor is created which grips bones along their edges and then applies an expansion force between the two bone edges. This expansionary force is used to encourage bone growth and elongation. Two clamps are used; each of the clamps is adapted to engage opposing edges of a bone. A rod extends from one clamp and presses against the other clamp; due to the threads on the clamp and the rod, a turn of the rod applies an expansion force between the two clamps. By selective application of this force, the bone naturally grows and elongates. The invention is particularly useful for craniofacial structures. Not only does the apparatus elongate the bone, but due to the nature of the clamping and forces applied over time, the adjacent soft tissue is also naturally elongated.

13 Claims, 4 Drawing Sheets

METHOD OF CRANIOFACIAL BONE DISTRACTION

BACKGROUND

This invention relates generally to surgical tools and more particularly to bone distractors.

Bone elongation by gradual distraction has proven beneficial in long bones. Thanks to the procedure, it is possible to elongate the superior or inferior extremity. This technique has been popularized by Ilizarov of Russia in the last few years.

While the elongation of the long bones has been successfully accomplished, elongation of the craniofacial bone structure has proven evasive.

The present pathology for elongation of the cranium or the face is particularly inadequate. Often defective growth of the maxillary mandible, forehead, or of the orbit is extremely difficult to correct. The techniques of hipoplasia or retrusion produce limited results when the bone being elongated is too short to provide the necessary basis for the procedure.

An associated problem also exists for the soft tissue where it is often too short or too insufficient for the procedure to be totally effective.

While these techniques produce "immediate" results on the whole, a more gradual growth inducement approach would generate better results and be more cosmetically pleasing.

It is clear that there is a significant need for efficient distractors which are as non-invasive as possible and which capitalize upon the body's natural growth capabilities.

SUMMARY OF THE INVENTION

The invention creates a bone distractor which grips bones along their edges and then applies an expansion force between the two bone edges. In this context, the preferred use of this invention involves the creation of a corticotomy or an osteotomy at the site for the enlargement of the bone.

The distractor of this invention is secured by clamps to the edges created by this surgical procedure. Preferably, these clamps have channels formed on one edge which are adapted to engage the edge of the bone. The size and shape of the channel is selected during design and manufacture to meet specific needs and bone sizes.

A threaded rod extends from one clamp and presses against the other clamp to apply a force between the two clamps. This expansionary force is used to encourage bone elongation.

In response to the force, over an extended period of time, sometimes on the order of a month or more, bone growth is established which tends to elongate the bone. This gradual growth of the bone is a natural occurring growth except that the direction and rate of growth is "steered" by the clamps and the amount of force applied between them.

This natural "slow" growth in the bone is matched by growth in the soft tissue as well. The simultaneous and balanced growth of both bone and soft tissue (i.e. skin, muscles, and tendons), results in a natural looking configuration once the growth level has been obtained.

The distractor of this invention is extremely simple in design. Two clamps are used; each of the clamps is adapted to engage opposing edges of a bone. Engagement with the bone edges is through the use of channels in the preferred embodiment. The channels form a smooth surface for nesting of the bone.

A rod extends from one clamp and presses against the other; due to the threads on the clamp and the rod, a turn of the rod applies an expansion force between the two clamps. The patient, often discharged from the hospital during this time, is instructed to turn the rod periodically (i.e. in the morning and night) a certain rotation. In practice it has been found that a quarter turn is sufficient to maintain a continuous growth of the bone at an appropriate rate.

By selective application of this force, the bone elongates. The invention is particularly useful for craniofacial structures.

As noted earlier, not only does the distractor of this invention elongate the bone, but due to the nature of the clamping and forces, the adjacent soft tissue is also naturally elongated. Hence, the distractor of this invention helps the craniofacial structures to elongate depending on the specific need of the patient and at the same time the distractor is elongating bone, it is also elongating the adjacent soft tissue.

The technique permits a reconstruction of the craniofacial skeletal defects without bone grafts, procedures of osteosynthesis, intermaxillar fixation and reduces the morbidity, operative time and days of hospitalization and is easy to control.

This distractor addresses a great many applications. For example, after removal of an eye due to retinoblastoma, in the aftermath growth stage, there is a hipoplasia of the orbit. This is due to the absence of pressure toward the front of the bone structures that would normally exist with the presence of an eye and muscles which at this point, have been removed.

Another application of this invention is in the area of preneosynostosis. In preneosynostosis, there is a premature bone closure of one or more sutras of the cranium.

Still another application of this distractor is in patients that have a cleft lip and palate. The closure of the lip and palate produce a scar which will act as a barrier on the exterior-posterior and transversal of the medial portion of the face which is also compromised by the short and somewhat tense soft palate.

In cases of retrognatia or Microsomia there is a lack of growth anterior-posterior transversal and vertical mandible which produces a discrepancy between maxilar and mandible, the lack of growth also affects soft tissue, skin, muscle and periosteum.

The technique permits a reconstruction of the craniofacial skeletal defects without bone grafts, procedures of osteosynthesis, intermaxillar fixation and reduces the morbidity, operative time and days of hospitalization and is easy to control.

The invention, together with various embodiments thereof, will be more fully explained by the attached drawings and the following descriptions.

DRAWINGS IN BRIEF

3

Figure 4:
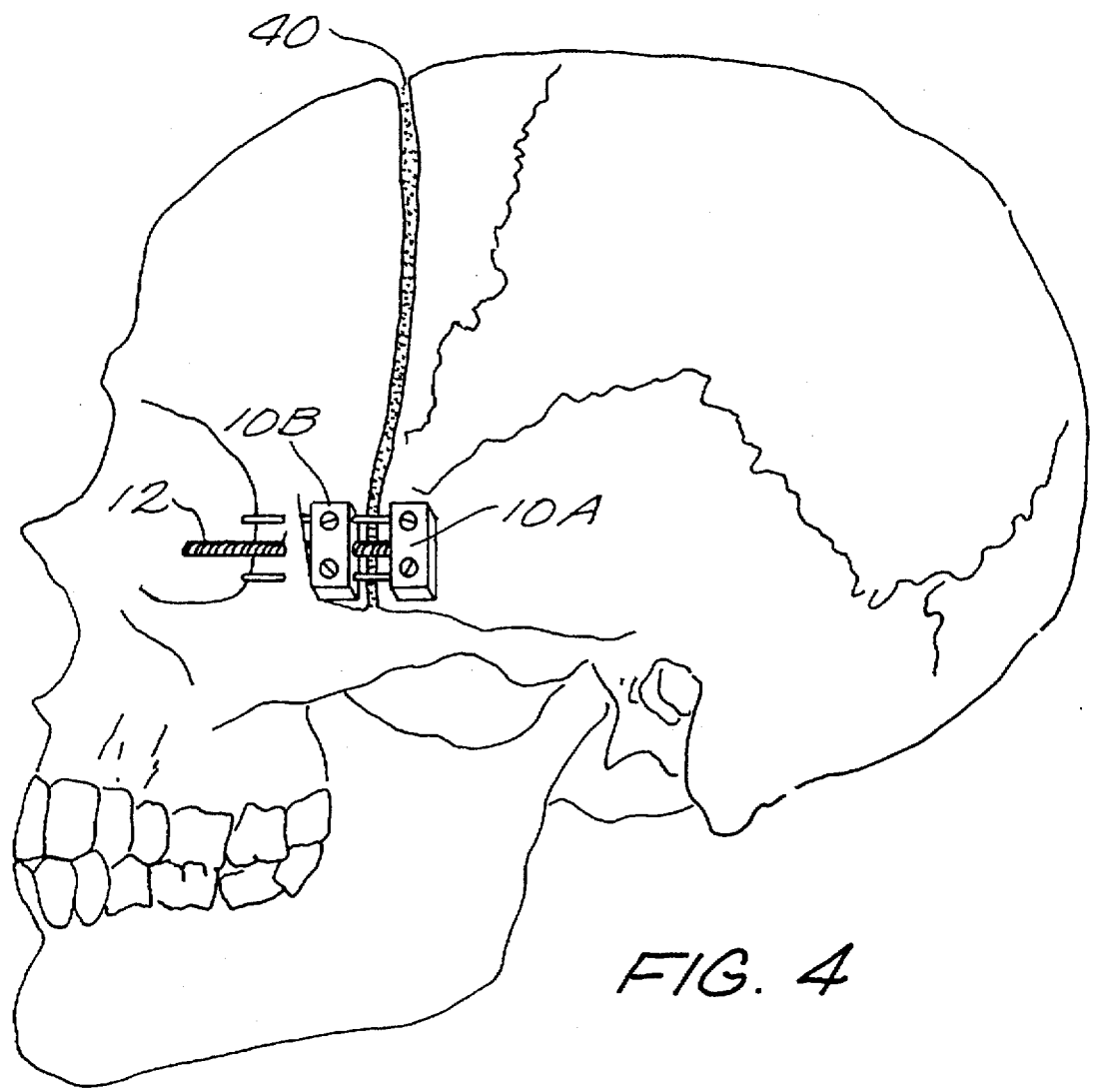

FIG. 4 is a view of the invention being used to elongate a portion of the cranium.

Figure 5:
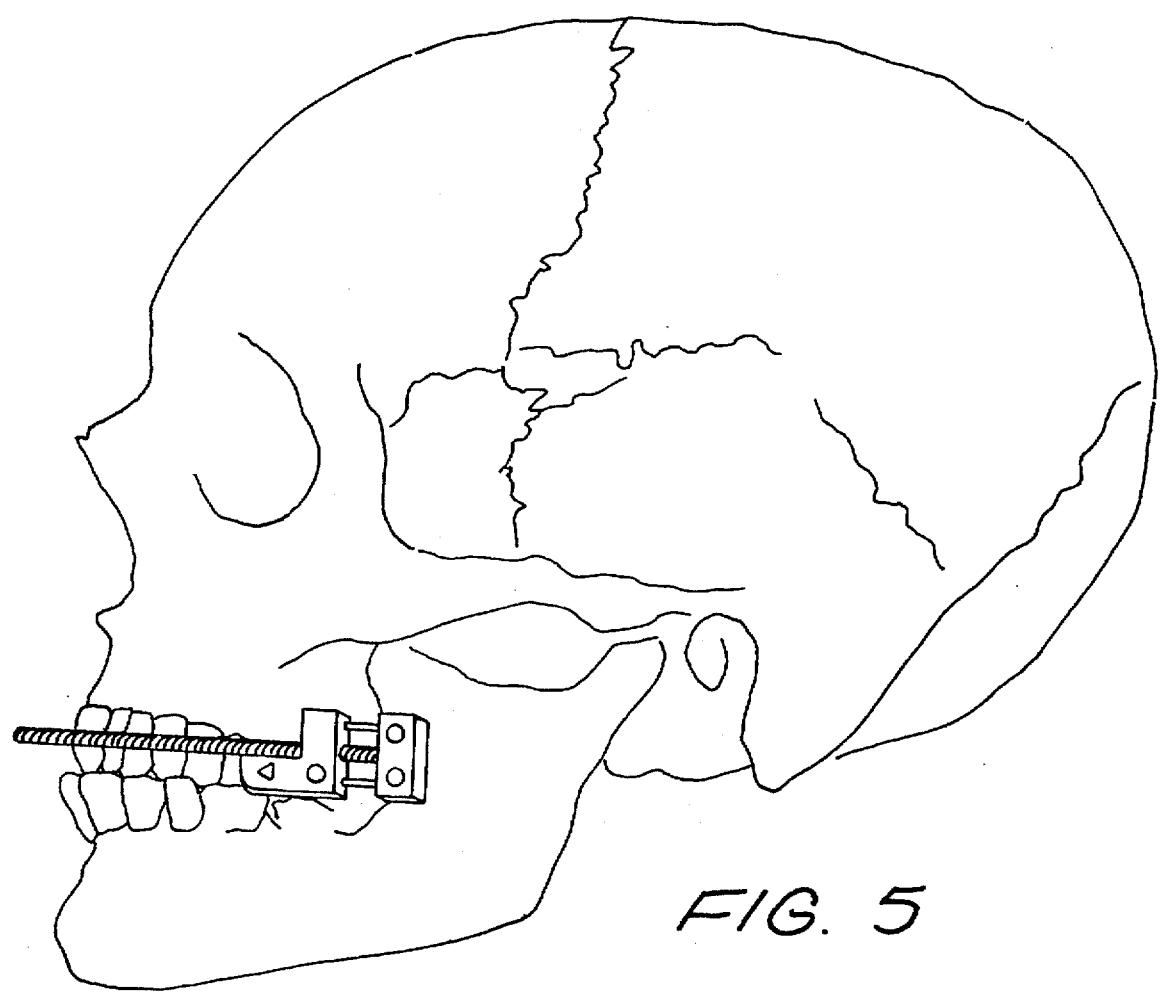

FIG. 5 is a view of the invention being used for modification of the structure of the teeth.

DRAWINGS IN DETAIL

Figure 1A:
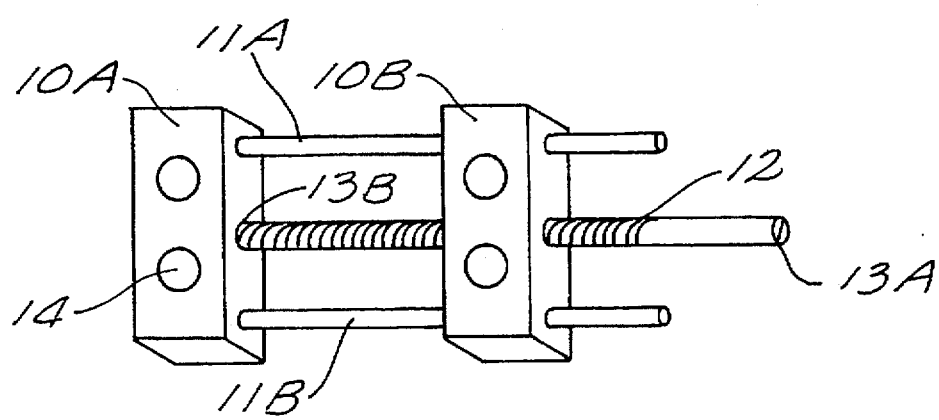
FIG. 1A is top view of the preferred embodiment of the invention.

FIG. 1A is top view of the preferred embodiment of the invention.

The distractor of this preferred embodiment uses two clamps 10A and 10B which are slideably connected via rods 11A and 11B. Rods 11A and 11B are connected to clamp 10A and extend through holes in clamp 10B. (An alternative embodiment attaches the rods to clamp 10B and slidably connects them to clamp 10A).

Clamp 10B has a threaded hole through which extends threaded rod 12. Threaded rod 12 has end 13B engage an anvil area of clamp 10A. Threaded rod 12 is selectively turned by the surgeon, a care-giver, or the patient by engaging a wrench with end 13A, which in this example, has a slotted end.

As threaded rod 12 is turned, an expansion force is proved between clamp 10A and clamp 10B. This in turn encourages bone growth between clamp 10A and clamp 10B. Threaded rod 12 is designed such that a complete turn (or rotation) makes a 1 mm elongation possible.

In this embodiment, holes are placed in clamps 10A and 10B, such as hole 14. These holes are optionally used for attaching clamps 10A and 10B to traditional bone pins or screws.

In the preferred embodiment, the whole devices is made of stainless steel; but, those of ordinary skill in the art readily recognize that this distractor can be manufactured from hardened silicone, hardened plastic, or any number of other materials.

Figure 1B:
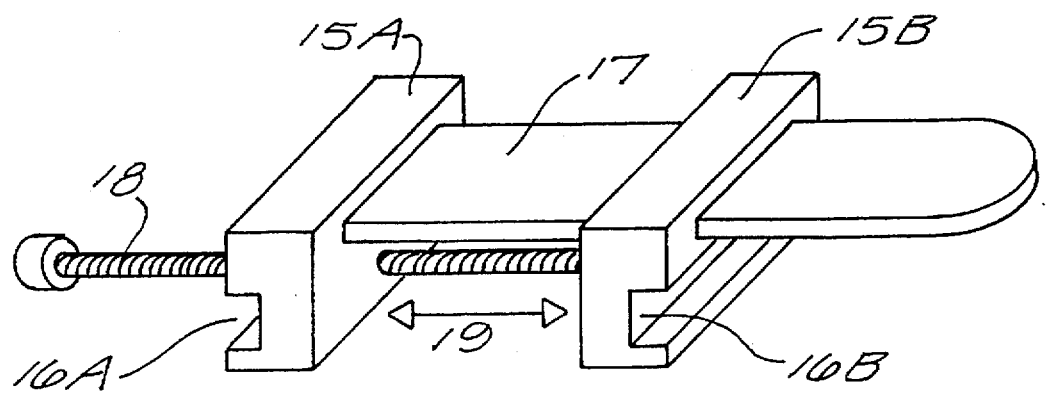
FIG. 1B is a perspective view of an alternative embodiment of the invention.

FIG. 1B is a perspective view of an alternative embodiment of the invention.

This view of this embodiment illustrates channels 16A and 16B of clamps 15A and 15B respectively. Channels 16A and 16B are adapted to accept edges of bone therein and then to apply an elongating force between the bone edges.

Clamps 15A and 15B, in this embodiment, are slidably connected via slide member 17 which is secured to clamp 15A and which extends through clamp 15B.

Threaded rod 18 is threaded through clamp 15A to press against clamp 15B and apply an expansion force as indicated by arrows 19.

As with the other embodiments, this expansionary force is applied over a long period of time, such as several weeks or more, to obtain both bone growth and a corresponding soft tissue growth. To accomplish this, the entire assembly is contained within the skin with the exception of the end of threaded rod 18, which is left exposed permitting the patient, or care-give, to selectively (such as twice a day) apply the expansionary force indicated by arrow 19.

This particular embodiment is useful in providing protection for the elongated site after the growth has been obtained. Once the growth has been obtained, since the assembly is constructed of benign material such as surgical steel, threaded rod 18 (which extends through the skin) is easily removed leaving the distractor in the bone area. Clamps 15A and 15B together with slide member 17 provide additional protection to the site from impact trauma.

Figure 1C:
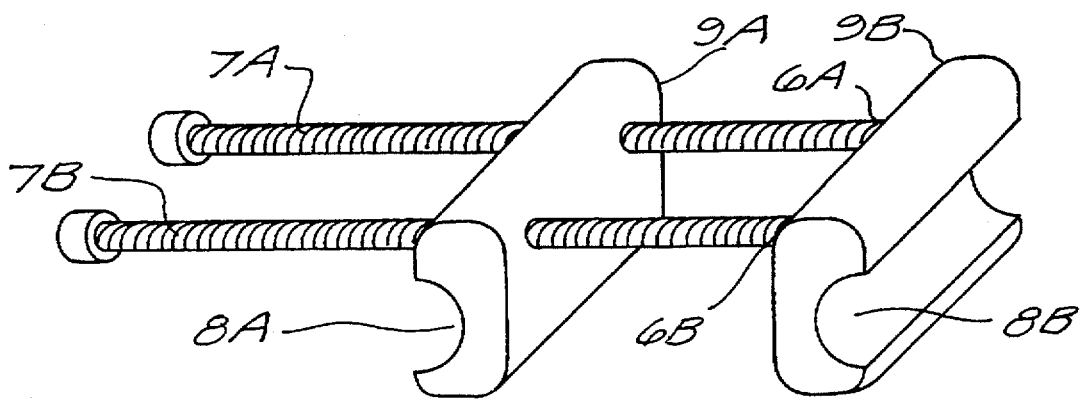
FIG. 1C is a perspective view of still another alternative embodiment of the invention.

FIG. 1C is a perspective view of still another alternative embodiment of the invention.

4

In this embodiment of the invention, the sliding member is eliminated between clamps 9A and 9B. Instead, two threaded members 7A and 7B are used to apply the expansionary pressure. In this embodiment, ends 6A and 6B are rotatably connected to clamp 9B to maintain the entire assembly as a single unit.

Clamps 9A and 9B are configured with channels 8A and 8B to engage the edge of the bone to be elongated.

This embodiment is particularly useful where straight elongation is not sought but where one side of the bone is to be elongated more than the other side.

Figure 2:
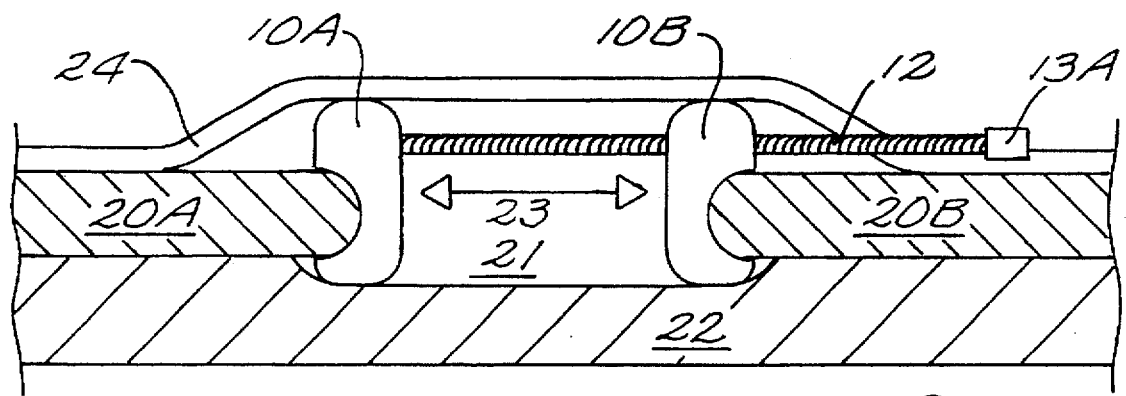
FIG. 2 is a side view of the preferred embodiment attached to a bone.

FIG. 2 is a side view of the preferred embodiment attached to a bone.

The first step in this procedure is the creation of a corticotomy which creates a gap 21 in the bone layer establishing side 20A and 20B. The corticotomy is not deep enough to affect the growth member 22 below the bone layer.

Clamps 10A and 10B are then positioned to engage bone sides 20A and 20B respectively. Threaded pin 12 is rotated to cause clamps 10A and 10B to move as indicated by arrows 23 and firmly engage these bone sides.

Skin layer 24 covers the entire distractor with the exception of end 13A which is left exposed for periodic adjustment by the surgeon, patient, or care-giver.

Figure 3:
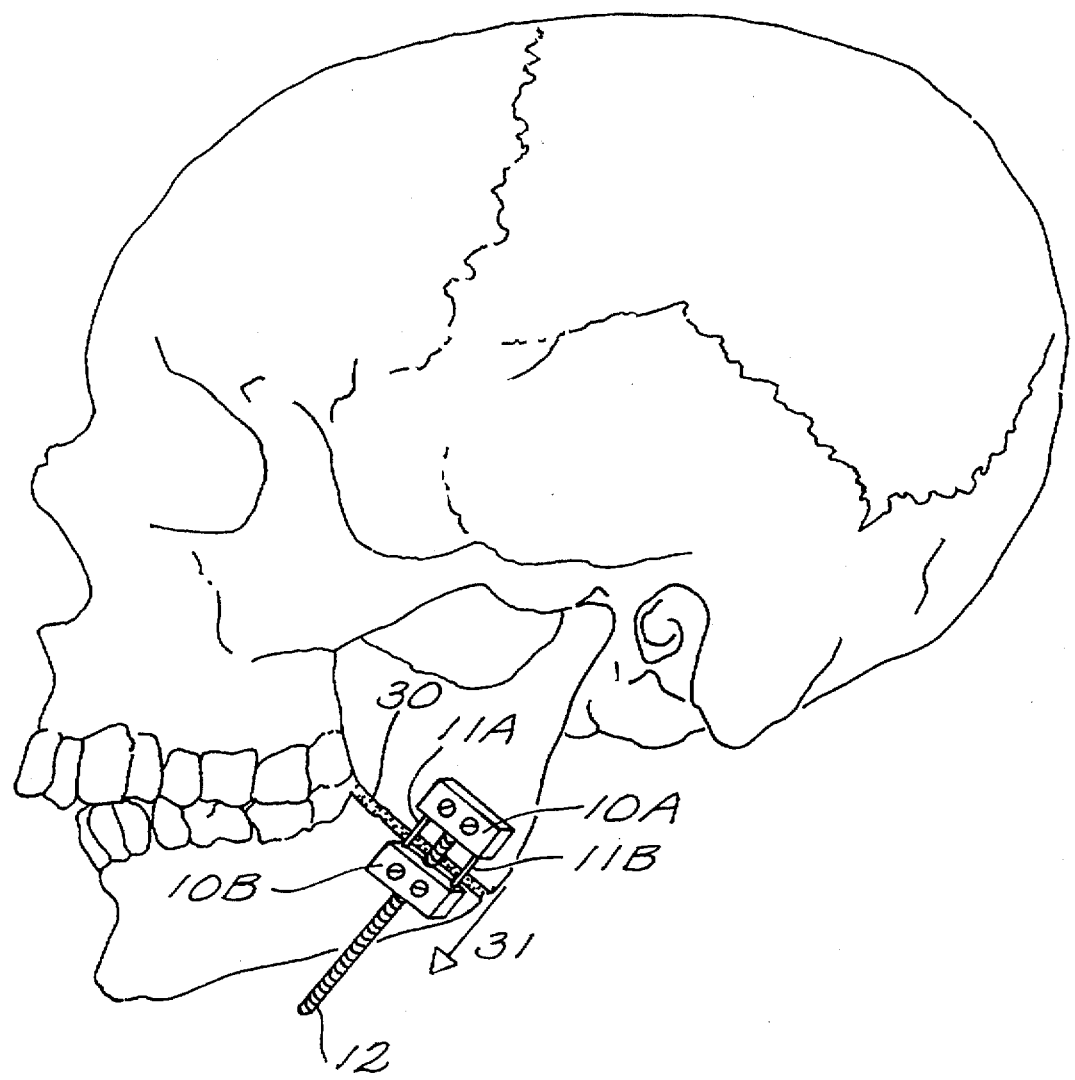
FIG. 3 is a view of the invention being used to elongate the mandible.

FIG. 3 is a view of the invention being used to elongate the mandible.

In these illustrations, the skin and muscles are not shown to better illustrate the procedure.

A corticotomy 30 is created in the external surface of the mandible in the area desired to be elongated. The depth of the corticotomy is of 1 mm or less and 2 mm of width.

The distractor is then fixed on the surface of the bone (clamps 10A and 10B) from one side to the other of the corticotomy. In this embodiment, the distractor is then reinforced by screws (two in each of the clamps) on the bone surface.

The two clamps 10A and 10B are then screwed into the bone and are united to each other by two pins 11A and 11B that maintain the parallelism of the clamps 10A and 10B. Pins 11A and 11B also maintain positioning for threaded rod 12.

Rotation of threaded rod 12 causes the clamps to expand as indicated by arrow 31. This simulates new bone growth where the corticotomy is performed and makes the bone increase it's length.

Generally the distractor is fixated with a 2 cm incision at the angular level of the mandible. Bone is reached in periosteum is elevated and the corticotomy is performed (a cut of the external cortical) in perpendicular direction in the same direction which the surgeon wishes to elongate the mandible. Once the distractor is in place, the activating screw, which is superimposed on the inferior border of the mandible and the rest of the distractor, is covered by soft tissue.

FIG. 4 is a view of the invention being used to elongate a portion of the cranium.

In the frontal-orbital advance, a osteotomy 40 is performed on the medial-lateral walls and on the base of the orbit. The osteotomy 40 continues to the frontal bone more or less parallel and in from of the coronal sutra. In the nasal frontal sutra, the nasal septum is liberated with extreme care to avoid lesioning (or hurting) the duramadre and the superior longitudinal sinus.

Once the osteotomy is completed, the distractor is fixated at the level of the temporal fossa and it is placed from one side to the other of the osteotomy 40 so that clamp 10A engage one side of the osteotomy while clamp 10B engages the other side of osteotomy.

At this stage, it is necessary to augment the osteotomy so the device can be put in closed, and in these cases the plate is not screwed to the bone because there is a double plate from one side to the other, connected by two screws that do not surface to the surface. This procedure's objective is to form no lesion to the duramadre from the intracranial side or soft tissues from the extracranial side. Small canals are made to permit the plates to enter laterally in the borders of the osteotomy.

Once the distractor is placed, the threaded rod 12 is introduced through the soft tissues so it can come out through the soft tissues of the lateral wall of the orbit, perpendicular to the superior orbital rim.

FIG. 5 is a view of the invention being used for modification of the structure of the teeth.

In the case of the maxilla, one group of patients that should have this procedure are patients with cleft lip and palate sequelae in which a maxilla advance or a facial advance is not possible due to the nature of the disease. There are two fragments of the maxilla which are difficult to stabilize after the osteotomy and the traditional advancement and also a non-gradual traction toward the palate tissues would produce a velofaringeal insufficiency and therefore would affect the patient's language (speech).

In these patients, a osteotomy type Leffort I or III, depending on each case, is performed with mobilization in the transoperative of the maxilla. The mucosa of the vestibular is closed and it is proceeded by the distractor and, also like the cranium of FIG. 4, to aid against the anterior border of the mandibular rim of the posterior part, small slits are done to introduce the screws laterally and the anterior part of the distractor placed. The distractor also fixates on the bands that have previously been secured at the level of the inferior molar. On the inferior molar is anchored a string that traps the inferior bar to the distractor with the object of the mandible not to open.

In general, the distractor is activated so it permits elongation at a rate of 1 mm a day. This elongation can continue for 6 to 8 weeks or more till the new bone is consolidated, then the distractor is removed.

This distractor is located under the soft tissues in close contact with the bone. This positioning results in comfort for the patients because it is practically invisible; also the scar that is produced by the distractor screw is minimal.

It is clear that the present invention creates a highly improved distractor which permits the selective elongation of bones.

What is claimed is:

1. A method of distracting craniofacial bone comprising the steps of:
   a) during a surgical step,
      1) in a submuscular surgical site, installing a bone dissector between two opposing edges of a craniofacial bone, and,
      2) via a threaded rod, engaging said bone dissector with said two opposing edges of craniofacial bone, and,
      3) exposing an end of said threaded rod through skin of a patient; and,
   b) in a post-operative step, via said threaded rod, periodically forcing said two opposing edges of craniofacial bone away from each other.

2. The method of distracting craniofacial bone according to claim 1, wherein the post-operative step includes the steps of:
   a) removing said threaded rod from the patient; and,
   b) permitting the skin of the patient to heal.

3. The method of distracting craniofacial bone according to claim 2, wherein the step of permitting the skin of the patient to heal includes the step of allowing said bone distractor to remain within said patient.

4. The method of distracting craniofacial bone according to claim 1, wherein the surgical step includes the step of, prior to the step of installing a bone dissector, the step of creating a fissure in said craniofacial bone.

5. A surgical method comprising the steps of:
   a) in a submuscular surgical site, installing a bone dissector between two opposing edges of a craniofacial bone;
   b) via a threaded rod, engaging said bone dissector with said two opposing edges of craniofacial bone; and,
   c) exposing a first end of said threaded rod through skin of a patient.

6. The surgical method according to claim 5, further including the step of, periodically forcing said two opposing edges of craniofacial bone away from each other.

7. The surgical method according to claim 6, further including the steps of:
   a) removing said threaded rod from the patient; and,
   b) permitting the skin of the patient to heal.

8. The surgical method according to claim 7, wherein the step of permitting the skin of the patient to heal includes the step of allowing said bone distractor to remain within said patient.

9. The surgical method according to claim 6, further including, prior to the step of installing a bone dissector, the step of creating a fissure in said craniofacial bone.

10. A bone dissection method comprising the steps of:
    a) in a submuscular surgical site, installing a bone dissector between two opposing edges of a craniofacial bone;
    b) via a threaded rod, engaging said bone dissector with said two opposing edges of craniofacial bone;
    c) exposing an end of said threaded rod through skin of a patient; and,
    d) periodically forcing said two opposing edges of craniofacial bone away from each other.

11. The bone dissection method according to claim 10, further including the steps of:
    a) removing said threaded rod from the patient; and,
    b) permitting the skin of the patient to heal.

12. The bone dissection method according to claim 11, wherein the step of permitting the skin of the patient to heal includes the step of allowing said bone distractor to remain within said patient.

13. The bone dissection method according to claim 10, further including, prior to the step of installing a bone dissector, the step of creating a fissure in said craniofacial bone.

* * * * *